(12) United States Patent
Casaña Giner et al.

(10) Patent No.: US 8,263,530 B2
(45) Date of Patent: Sep. 11, 2012

(54) AGROCHEMICAL FORMULATIONS CONTAINING MICROCAPSULES

(75) Inventors: Victor Casaña Giner, Ebenfurth (AT); Miguel Gimeno Sierra, Ebenfurth (AT); Barbara Gimeno Sierra, Ebenfurth (AT)

(73) Assignee: GAT Microencapsulation AG (AT)

( * ) Notice: Subject to any disclaimer, the term of this patent is extended or adjusted under 35 U.S.C. 154(b) by 498 days.

(21) Appl. No.: 12/312,644

(22) PCT Filed: Nov. 21, 2007

(86) PCT No.: PCT/EP2007/010073
§ 371 (c)(1),
(2), (4) Date: May 18, 2009

(87) PCT Pub. No.: WO2008/061721
PCT Pub. Date: May 29, 2008

(65) Prior Publication Data
US 2010/0056373 A1    Mar. 4, 2010

(30) Foreign Application Priority Data

Nov. 23, 2006 (EP) .................................. 06024299

(51) Int. Cl.
*A01N 25/28* (2006.01)
*A01N 57/00* (2006.01)
*A01N 43/00* (2006.01)
*A01N 43/64* (2006.01)
*A01N 47/28* (2006.01)

(52) U.S. Cl. ........ 504/359; 504/127; 504/130; 504/133; 504/327

(58) Field of Classification Search .................. 504/127, 504/130, 133, 327, 359
See application file for complete search history.

(56) References Cited

U.S. PATENT DOCUMENTS

| 4,938,797 A | * | 7/1990 | Hasslin et al. | 504/359 |
| 5,049,182 A | * | 9/1991 | Scher et al. | 504/149 |
| 5,460,817 A | | 10/1995 | Langley et al. | |
| 5,549,903 A | * | 8/1996 | Marcus | 424/408 |
| 5,929,053 A | * | 7/1999 | Murakami et al. | 514/89 |
| 6,693,063 B2 | * | 2/2004 | Schnabel et al. | 504/310 |

FOREIGN PATENT DOCUMENTS

| WO | WO 0224798 A2 | * | 3/2002 |
| WO | WO 02/49432 A1 | | 6/2002 |
| WO | WO 2008/061721 A3 | | 5/2008 |

OTHER PUBLICATIONS

Herbert, Richard M., Database CA, Chemical Abstracts Service, Novel polymeric dispersants for aqueous suspension . . . , XP002431165, (2002).
Database WPI Week 199521, Thomson Scientific, London, GB; an 1995-158855, XP002431168.
Database WPI Week 200453, Thomson Scientific, London, GB; an 2004-546815, XP002431169.

* cited by examiner

*Primary Examiner* — Johann Richter
*Assistant Examiner* — Andriae M Holt
(74) *Attorney, Agent, or Firm* — Vedder Price PC

(57) ABSTRACT

The invention refers a new formulation of fluoroxypyr or chlorpyrifos or diflufenican microencapsulated and in the form of water dispersable granules or as a part of a ZC formulation. Further the invention refers to water dispersable granules containing microcapsules that enclose fluoroxypyr and at the same time the WDG have also sulfonylureas outside of the microcapsules. Further we provide formulations in the form of SC or ZC of the aforementioned active ingredients and its combinations. Also fluoroxypyr may be replaced by any agrochemical of any biological activity that is solid at room temperature and melts below 110° C. Mixtures of actives of such formulations are also contemplated.

12 Claims, No Drawings

AGROCHEMICAL FORMULATIONS CONTAINING MICROCAPSULES

STATE OF THE ART

It is known that microencapsulation is a technique that offers a number of advantages in front of other formulation techniques in the field of Agrochemistry. Modern agricultural practice requires controlling the application of biological active components to the target. This allows: to increase compounds stability over extended periods of time, to reduce environmental hazards, to decrease acute toxicity, and to deal with incompatibility between ingredients. Fluids are used as functional inerts in high technology formulations, e.g. allowing encapsulation of solid active ingredients and adjusting the diffusion rate of the active substance.

Several basic processes have also been disclosed, that can be divided into coacervaion, interfacial polymerization and in-situ polymerization. Most commercially available CS (microcapsule suspension) formulations are manufactured by interfacial polymerisation, e.g.: Chlorpyrifos CS, Lambdacyhalothrin CS, Fluorochloridone CS, and Methylparathion CS. When dried, they may form water dispersable granules containing microcapsules. A typical method of CS manufacture by interfacial polymerisation is to dissolve the active ingredient, monomers or prepolymers in a fluid (oil phase). The latter is dispersed into the water phase, which contains emulsifiers, protective colloids (and eventually additional prepolymers). The capsule wall around the oil droplet is formed by polymerisation at the interface of water and oil in the presence of a catalyst or by heat.

Many wall-forming materials are available for the encapsulation of liquid or solid active ingredients. The release rate of the latter can be adjusted by selecting the optimum
  wall materials,
  dimensions of the microcapsules (diameter and wall thickness),
  porosity of the wall (degree of cross-linking),
  protective colloid(s),
  fluids (in oil or in water).

Fluids (solvents), in addition to their ingredients dissolving role, are influencing the emulsion quality by maintaining a low viscosity during the emulsification and polymerization steps.

No prior art leads to an obvious solution for the problem addressed in this invention (basic unitary process for different formulation types and mixtures of active ingredients).

DESCRIPTION

On of the most difficult tasks to achieve is to get capsule suspensions or water dispersable granules (WG) formed with microcapsules in common process for herbicides, fungicides and insecticides, and their mixtures—both of activity and different active ingredients—in such a way that this process facilitates the industrial production of such agrochemicals because of the use of the same technology and the same process, and, basically the same coformulants. We have been unable, for the first time ever to find a common microencapsulation and spray dry process not only for encapsulation of different types of molecules but also incompatible molecules that up to now, no Company has been able to apply in an Industrial way. Therefore the scope of this invention is to facilitate the production of agrochemical formulations in the form of capsule suspension (CS) and/or ZC and/or WG in a unified production process. Also is object of the invention to protect the microcapsules, CS, ZC and WG formulations of active ingredients never encapsulated before in these type of formulations and also the process characterized in that selected coformulants, wall forming materials are both able to reach a CS formulation and, at the desire of the producer, to proceed further without essential changes to spray dry this CS to form a WG of microcapsules. Further, our novel process allows combinations not possible o market until now, as is the case of mixtures of fluoroxypyr with sulfonylureas of an kind (this was not possible before due to chemical incompatibility and also due to the proper selection of coformulants that allow the stability of both type of ingredients, and a functionally good formulation with excellent dispersibility properties.

For example, according to prior art we have hardy tried make WG of microencapsulated fluoroxypyr using the known methods of making WG of chlorpyryfos (both processes of Beestman and Muliqueen-Monsanto and Dow-), with unsuccessful results. In both cases we obtain a wet sieving residue of more than 10%, of which 50% corresponds to crystallized fluoroxypyr outside of the microcapsules This is easily understood insofar, the formulation technology is a very complex chemistry field, where many parameters influence at the same time: compatibility of active ingredients with the wall forming materials, surfactants, coformulants, temperature of granulation, etc.

At the view of the state of the art, it is not obvious how to microencapsulate fluoroxypyr, a fact that is confirmed by the non-existence of any microencapsulated fluoroxypyr available in the marked anywhere in the world. The selection of the wall forming materials, the conditions of the reaction and, extremely important, the coformulants can only be achieved after a long period of extensive research involving novel ideas not available before. Also, it is described in an enable disclosure for the first time how to microencapsulate fluoroxypyr, add a sulfonylurea and spray dry to obtain a novel combination of fluoroxypyr and sulfoylureas (also chlorpyrifos and sulfonyureas). For incorporation of sulfonylureas plus other actives microencapsulated, according the present invention they are milled to form a suspension concentrate (SC), and then the CS suspension is added to the SC. Optionally the SC contain other sulfonylurea-compatible agrochemicals and optionally the microcapsules contain a mixture of several acives compatible in between them. One of the novelty aspects of this invention is the ability to have an "oil phase" (inside microcapsules) where the only requisite is that in such phase the oil soluble materials are compatible, and a "water phase" where the same requisite applies, but it is not necessary that the oil soluble actives and the water soluble acives are compatible in between them.

In fact, the present invention has its more powerful sense when the active ingredients in and out—of the microcapsules—are incompatible in the broad sense, namely, that the activity is reduced because any reason including chemical reaction in between incompatible materials, adsorption, crystallization induction, etc.

Chlorpyrifos microcapsules in the form of water dispersable granules are known from a number of patents of Dow and Monsanto. However, the processes so far disclosed differ in the process of the present invention. We have invented new ingredient lists where the functionality and role of essential coformulants that unexpected properties and as well the use of a water-insoluble catalyst in the form of an emulsion to control the speed and degree of polymerization of the microcapsule's wall, and the improved dispersibility and suspensibility of the present formulation when compared to the prior art. Also, the use of our wall forming materials lead to a taylor made release rate, easier to predict and control than when conventional microencapsulating techniques are used.

Fluoroxypyr on the other side has never been described in microencapsulated form, at least in a enable disclosure, and lesser having the extraordinary formulation properties described herein regarding also particle size, and long term stability, and when in WG (CS) formulation, the high dispersibility and suspensibility properties

DETAILED DESCRIPTION OF THE INVENTION

For the purpose of the Invention, the preferred materials are those having a low melting point as one of the materials to microencapsulate, at least one of the actives (if chosen to be more than one) to be inside the microcapsules. Outside of the microcapsules, optionally it is used a sulfonylurea or any suitable agrochemical. The invention is better understood with examples.

Example 1

A typical composition to microencapsulate would be, for fluoroxypyr, as follows (in w/w %):

| | |
|---|---|
| Fluroxypyr ester (meptyl, 2-butoxymethylethyl, etc.) | 50.0 |
| PAPI/Desmodur 44 V 20 L | 3.50 |
| PowderLink 1174(40% in g-Butyrolactone) | 1.25 |
| Water Phase | |
| Synperonic PE/64 | 0.60 |
| Metasperse 500 L | 10.00 |
| Citric Acid | 0.14 |
| Catalyst(Triethyl amine 20% emulsion) | 0.25 |
| Water | 34.26 |

Both water and oil phases are warmed up to about 70-80° C., in order to have the active ingredient in liquid form (in this case fluoroxypyr, in other cases, this temperature may be higher or lower according the melting point). Although inclusion of solid acives or coformulants is possible we do not enter into detail for the sake of simplicity.

Up to this step we can find enormous differences with respect to prior art. Some processes, instead of using the warming step, use the dissolution with Solvesso (patent documents of Monsanto on Chlorpyrifos, for example). This has the disadvantage that at the end of the spraying dry step (if this "single process technique is used"), the solvesso is partially evaporated due to the hot conditions of spray drying, leading to an increased unencapsulated material and increase of crystals outside of the microcapsules. Other processes, as those of Dow for Chlopyrifos, have the inconvenience that the surfactant/dispersant systems reach the cloud point and then those documents do not enable the use of a single unique process that allows to stop at the time of the CS formation, or proceed further with an spray-dry to create WG or even to produce a mixture formulation of suspension concentrate+capsule suspension (ZC formulation).

To be able to have a "standard processmulti-purpose" is needed that the surfactant system (including dispersants and wettings) has two properties: 1) be able to be stable at a wide range of pHs, to be able to be used for encapsulation of different actives and 2) have a cloud point over the melting point of the desired agrochemical to encapsulate, concomitantly, preventing phase inversion during the process.

We have surpressively found that indeed exist such surfactant systems, in particular those based in the use of the Metasperse 500L or Metasperse 550S type of dispersant and a Symperonic PE/64 surfactant-wetting agent. Other options to replace the Symperonic PE/64 are ethoxylated/popoxylated alcohols, such Tergitol 15-S (secondary alcohol series), Tergitol TMN (ramified) or Tergitol XD or XDLW (EO/PO copolymers). These alcohols (ethoxylated and/or propoxlated) are selected according a cloud point over the temperature used for melting the active ingredient, that in the case of fluoxypyr is about 75° C. Regarding the Metasperse 500 series, we have not found any other better dispersant for the purposes of both being able to have a good CS suspension, to spray dry it and have a good WG formulation or to mix with an SC to have a good ZC formulation. Further we have found amazingly that the properties of Atlox Metasperse 500L in order to prevent Ostwald ripening forces and agglomeration processes is valid for all formulations of the type CS, ZC and WG (of capsules), making our desired target of an "unified" process for different formulation times a reality. In particular, and referring to chemical properties rather than to brand names (Metasperse 500L, 550S), the type of compounds preferred are styrene acrylic polymers, but more preferentially, and with evident better performance anionically substituted styrene acrylic polymers, being this anionic substituents being chosen from a wide range, preferably, but not necessarily from sulphonates and phosphates.

Regarding the process, both mentioned phases are mixed (emulsionated) at a suitable speed of an ultraturrax type mixer (e.g., 2000 rpm) for a short time (e.g., 10 minutes), adding the catalizator short after the emulsification step begins (e.g., 1 to 3 minutes) till obtaining a particle size of about 1 to 30 μm, being obvious that other sizes may be selected. Then a cooking process is initiated, for some hours (typically 2 h), and the capsules are hardened. A cooling and filtering step follows to obtain a agriculturally suitable CS formulation of fluoroxypyr (or of any other agrochemical that is solid at room temperature and with a low melting point—below about 110° C., as far as the surfactant does not reach the cloud point).

According to the spirit of the invention, we are able to proceed with this "ready to use" formulation to form a ZC formulation. This can be easily achieved by providing a customary SC of a suitable agrochemical, particularly important a sulfonylurea or mixtures thereof, for example metsulfuronmethyl. An example of the composition of the metsulfuronmethy concentrate is:

| Ingredient (metsulfuron conc.) | |
|---|---|
| water | 34.02 |
| Metasperse 500 L | 26.74 |
| Geropon DOS/PG | 5.40 |
| Dispersing Agent LFH | 0.49 |
| Antifoam | 0.26 |
| Metsulfuron techn. | 33.09 |
| SUM | 100.00 |

Both the fluoroxypyr CS and the methsulfuron-methyl SC may be mixed in the desired proportion to obtain the desired final formulation of acive ingredients, having the metsulfuron-methyl SC the necessary coformulants for a perfect formulation stability.

To be more explicit, a ZC formulation Fluoroxypyr+Metsulfuron can be done according the process described with the following ingredients:

| Ingredient (water phase) | |
| --- | --- |
| Synperonic PE/L64 (pure) | 0.23 |
| Metaspherse 500 L (30%) | 3.85 |
| Citric acid | 0.05 |
| Catalysator (dibutyltin laurathe) | 0.10 |
| Water | 13.18 |
| SUM | 17.41 |
| (Oil phase) | |
| Fluroxypyr-ester | 19.23 |
| PAPI/Desmodur 44 V 20 L | 1.35 |
| Powderlink 1174 (40% in g-Butyrolactone) | 0.48 |
| SUM | 21.06 |
| Ingredient (adjustment mix) | |
| Metaspherse 500 L (30%) | 16.45 |
| Geropon DOS/PG | 3.32 |
| Dispersing Agent LFH | 0.30 |
| Antifoam | 0.16 |
| Urea | 18.40 |
| Metsulfuron conc. (~31%) | 1.97 |
| water | 20.93 |
| SUM | 61.53 |
| TOTAL | 100.00 |

Final: 38.47 wt % Fluroxypyr CC
61.53 wt % Adjustmend mix

If the desire is to make a WG from the CS obtained above (fluoroxypyr CS, optionally other actves replacing/added to the oil phase) or from the ZC mentioned just above these lines, then the mixture must be adjusted for the purposes of spray drying. We have invented a surpesively easy solution to prepare the CS or the ZC for the spray drying step. The content of the styrene acrylic polymer may vary in between 1 to 45% in w/w in the final formulation.

This consists on the addition to the water phase, in which the microcapsules are suspended of a further quantity of Metasperse 500 Series (or any similar dispersant type of the same chemical class (modified styrene acrylic polymer or anionically modified styrene acrylic polymer, more preferably of the second class) in an amount of 2 to 20% in w/w related to total weight of liquid to spray and from 0.1 to 15% of any sulfosuccynate available in catalogs for the agrochemical industry (e.g., Clariant, Uniquema, Cognis, etc) or similar type of chemical.

Then the product is spray dried at a temperature of the product slightly below the melting point (e.g., for Chlopyrifos 35° C., for the example above 40-45° C.) and a temperature of the air of 70-75%. Normally the WG consisting of microcapsules is deemed to be enough dried when the humidity is below 0.5%.

Therefore, we have shown how following a common process a fluoroxypyr CS may be converted into a ZC without any particular changes directed in the process of making the CS, and the same to end up with a WG of fluoroxypyr and metsulfuon.

One of the main targets of the combination of microencapsulated material mixed with unencapsulated materials is to achieve a longer stability of the most labile compound.

A test on the storage stability was performed with the following results:

| Content of active ingredient [wt-%, g/kg] of water dispersible granules of Fluroxypyr 250 g/kg + Metsulfuron 10 g/kg WG - Generic Name: FXY + MET 26 WG | | | | | |
| --- | --- | --- | --- | --- | --- |
| GAT Registration ID | | divided in five portions | | | |
| Number Test Item ID Number[1] Content of A.I. | FXY- MSF_0604 | GLASS[1] 54 ± 2° C., after storage | PLASTIC[2] 54 ± 2° C., after storage | GLASS[3] 0 ± 2° C., after storage | PLASTIC[4] 0 ± 2° C., after storage |
| Fluroxypyr wt-% | 39.37 | 38.57 | 38.35 | 38.65 | 38.51 |
| Metsulfuron wt-% | 1.18 | 1.18 | 1.18 | 1.18 | 1.19 |

Comparison of stability of fluoroxypyr and metsulfuon-methyl when a WG granulation is made according to U.S. Pat. No. 5,688,743 (Dow) and the encapsulation step has been omitted and replaced by a joint milling of the corresponding amount of fluoroxypyr and metsulfuron-methyl:

| Content of active ingredient [wt-%, g/kg] of water dispersible granules of Fluroxypyr 250 g/kg + Metsulfuron 10 g/kg WG - WHITOUT MICROENCAPSULATION OF FLUROXYPYR | | | | | |
| --- | --- | --- | --- | --- | --- |
| GAT Registration ID | | divided in five portions | | | |
| Number Test Item ID Number[1] Content of A.I. | FXY- MSF_060/ | GLASS[1] 54 ± 2° C., after storage | PLASTIC[2] 54 ± 2° C., after storage | GLASS[3] 0 ± 2° C., after storage | PLASTIC[4] 0 ± 2° C., after storage |
| Fluroxypyr wt-% | 39.41 | 28.02 | 16.05 | 34.44 | 36.34 |
| Metsulfuron wt-% | 1.16 | 0.21 | 0.24 | 0.35 | 0.39 |

As we can see from the table above, the incompatibility of metsulfuron-methyl is obvious, leading to an unusable water dispersable granule because of loss of active ingredient. Fluoroxypyr, to certain extent, also degradates: the fact that in cold fluoroxypyr is reasonably well conserved means that in a non-microencapsulated flurosypyr WDG (with a sulfonylurea) the reaction of degradation takes place on the finished product, and not during the production of the WG.

Results on physicochemical properties of water dispersible granules of Fluroxypyr 250 g/kg + Metsulfuron 10 g/kg WG - Generic Name: FXY + MET 26 WG

| | | divided in five portions | | | |
|---|---|---|---|---|---|
| GAT Registration ID Number Test Item ID Number[1] | FXY-MSF_0604 | GLASS[1] 54 ± 2° C., after storage | PLASTIC[2] 54 ± 2° C., after storage | GLASS[3] 0 ± 2° C., after storage | PLASTIC[4] 0 ± 2° C., after storage |
| pH value$_{(20° C.)}$ | 6.6 | 6.8 | 6.8 | 6.8 | 6.8 |
| Tap density[3]$_{(20° C.)}$ [g/cm$^3$] | 0.590 | 0.577 | 0.585 | 0.566 | 0.592 |
| Particle size [μm] | | | | | |
| D (v, 0.5) | 8.18 | 8.18 | 7.82 | 7.85 | 8.08 |
| D (v, 0.9) | 20.56 | 20.44 | 20.15 | 21.27 | 21.52 |
| Suspensibility [wt-%] | 82 | 84 | 83 | 80 | 81 |
| Dispersibility [wt-%] | 94 | 99 | 99 | 97 | 97 |
| Wettability [sec] | 0 | 0 | 0 | 0 | 0 |
| Persistent foam [mL] | 0 | 0 | 0 | 0 | 0 |

One of the most suppressive aspects of the invention is the inclusion as a best choice dispersant the anionically modified styrene acrylic polymers. This class of surfactants shows to:
1—Provide a very good dispersion of the microcapsules
2—Provide a perfect compatibility with an SC, where the same polymer can be used as a dispersant.
3—Provide an exceptional granule's coformulant that improves the dispersibility over WG of microcapsules produced with state of the art techniques.

To illustrate this, we show how the invention can be used for the production of microencapsulated chlorpyrifos, adding to the CS formulation (ready to use in the field as such) some "helpers" (included in the second adjustment mixture) for the granulating step and obtaining very high dispersible granules with low wet sieven residue, and very important almost unappreciable unencapsulated material.

Example 2

The formulation of Chlorpyrifos 750 g/kg WG (CS) consists of two components, a capsule suspension and an adjustment mixture. The capsule suspension works as base for different formulations depending on the adjustment, like 240 g/L CS, 400 g/L CS and 750 g/kg WG. The target is to achieve both a "ready to use" CS formulation, and for the customers interested in having a WG (CS), to be able to use the same produced CS and proceed to spray dry. For development of the given formula of Chlorpyrifos 75 WG (CS) two hundred capsule suspensions have been done during the development, being adjusted with hundred eighty different adjustment mixtures. Only those formulations containing styrene acrylic polymers, and particularly phosphated and/or sulphated substituted styrene acrylic polymers are improving state of the art formulations of Chlorpyrifos 700 g/kg. The formulation with best results is as follows:

| Recipe for Chlorpyrifos capsule supension | | |
|---|---|---|
| CPP01CS202 | Amount in weight percent [wt-%] | |
| Oil Phase | 100 | 55.75 |
| Chlorpyrifos technical (calculated as 99%) | 91.48 (90.57) | 51.00 (50.49) |

-continued

| Recipe for Chlorpyrifos capsule supension | | |
|---|---|---|
| CPP01CS202 | Amount in weight percent [wt-%] | |
| Chlorpyrifos impurities (calculated as 1%) | (0.91) | (0.51) |
| Desmodur 44 V 20 L/PAPI | 6.28 | 3.5 |
| Crosslinker | 2.24 | 1.25 |
| Water Phase | 100 | 44.00 |
| Water | 77.14 | 33.94 |
| Symperonic PE/L64 | 1.36 | 0.60 |
| Metasperse 500 L | 21.20 | 9.33 |
| Citric acid | 0.30 | 0.13 |
| Catalyst | | 0.25 |

The catalyst may be for procedural reasons to be dibutyltinlaurate, but the best control of the reaction is achieved by an emulsified catalyst (not soluble in water, but emulsified in it, a concept completely new). Some details to handle this unique type of catalyst in the microencapsulation field is that The components of the Catalyst are mixed together using an ultrasonic bath or Ultrathurrax to homogenize in no special order at room temperature. Care has to be taken that the catalyst will separate within 24 hours and therefore should be homogenized prior to addition of the catalyst was prepared by mixing the components for 100 mL (water, Symperonic PE/L64, Triethylamine) by simple shaking in a bottle. In fact the catalyst in chemical sense is the triethylamine, but the real "catalyst" in the practice is this emulsion (comparable to platinum alone and platinum in carbon support).

Recipe for the Catalyst in Chlorpyrifos capsule supension

| Catalyst | Amount in weight percent [wt-%] |
| --- | --- |
| Triethylamine | 20 |
| Synperonic PE/L64 | 1 |
| Water | 79 |

Recipe for Chlorpyrlfos ready to use capsule suspension

| CPP01CS202GD | | Amount in weight percent [wt-%] |
| --- | --- | --- |
| Capsule suspension | 100 | 83.07 |
| Chlorpyrifos technical (calculated as 99%) | 51.00 (50.49) | 42.36 (41.94) |
| Chlorpyrifos impurities (calculated as 1%) | (0.51) | (0.42) |
| Desmodur 44 V 20 L/PAPI | 3.5 | 2.91 |
| Crosslinker (Tetraethoxyethyl glcoluril in 40% cyclohexanone) | 1.25 | 1.04 |
| Water | 33.94 | 28.19 |
| Symperonic PE/L64 | 0.60 | 0.50 |
| Metasperse 500 L | 9.33 | 7.75 |
| Citric acid | 0.13 | 0.11 |
| Catalyst | 0.25 | 0.21 |
| Adjustment mixture GD | 100 | 16.93 |
| Metasperse 500 L | 76.60 | 12.97 |
| Antifoam TEGO MR2138 | 1.00 | 0.17 |
| Dispersing agent LFH | 1.80 | 0.30 |
| Geropon DOS/PG | 20.60 | 3.49 |

Further is we want to spray dry this CS formulation of chlorpyrifos, we proceed as follows in the spray drier:

Typical Parameters for spray drying of Chlorpyrifos adjusted capsule suspension

| CPP01CS202GD Aeromatic MP1 | | initial Parameters |
| --- | --- | --- |
| Nozzle Diameter | | 2.0 mm |
| Air pressure | | set to 2.0 bar |
| Temperature (incoming air) | | set to 60° C. |
| Vent level, air in | | 50% |
| Vent level, air out | | 55% |
| Feed rate | | 15 g/min |
| Parameter | Range | typical Value |
| Temperature (incoming Air) | 41° C.-52° C. | 46° C. |
| Temperature (Product) | 38° C.-44° C. | 40° C. |
| Temperature (leaving Air) | 32° C.-38° C. | 35° C. |
| Pump Feed | 15 g/min to 94 g/min | 40 g/min |

The resulting product has the following specifications:

TABLE 1

Specifications for Chlorpyrifos 750 g/kg WG

| Parameter | Unit | Method | Specification |
| --- | --- | --- | --- |
| Chlorpyrifos | wt-% | GAT-0906-CPS01-GC | 72.50-77.50 |
| Clorpyrifos | g/kg | GAT-0906-CPS01-GC | 725.0-775.0 |
| Appearance | | Visual | White to slightly brown granules |
| Water content | g/kg | CIPAC MT 30.5 | <15 |
| Particle size D(v, 0.5) | μm | CIPAC MT 187 | 2.0-4.0 |
| Particle size D(v, 0.9) | μm | CIPAC MT 187 | <50 |

TABLE 1-continued

Specifications for Chlorpyrifos 750 g/kg WG

| Parameter | Unit | Method | Specification |
| --- | --- | --- | --- |
| Particle size D(v, 0.5) | μm | CIPAC MT 187, 2 min sonification | 2.0-4.0 |
| Particle size D(v, 0.9) | μm | CIPAC MT 187, 2 min sonification | <15 |
| Granule size | mm | CIPAC MT 59 | 0.2 < x < 1.0 |
| pH value | | CIPAC MT 75.3 | 6.0-7.0 |
| Persistent foam | mL | CIPAC MT 47.1 | ≦3 |
| Suspensibility | % | CIPAC MT 184 | >90 |
| Dispersibility | % | CIPAC MT 174 | >95 |
| Wettability | sec | CIPAC MT 53.3.1 | <30 |
| Wet Sieving | % | CIPAC MT 59 | <0.1 |

The extraordinary values on suspensibility and dispersibility are well ahead of the current state of the art in chlorpyrifos WG at high load (60-80% g/kg). The inventors have only achieved this result thanks to the unexpected properties of the (optionally anionically substituted) styrene acrylic polymers.

Important to say, any other formulation do no containing styrene acrylic polymers as in the formulation yielded a product below FAO specifications, in particular regarding suspensibility (<50%), dispersibility (<10%) and wet sieving residue (>5%).

The examples show how chlorpyrifos, fluoroxypyr and metsulfuron-methyl are greatly benefited from the present invention. It is clear that any sulfonylurea would be protected as well when combined with fluoroxypyr or any other agrochemical with similar characteristics regarding melting point.

We have also performed the microencapsulation as above described with diflufenican alone and in combination with nicosulfuron, with the same good results.

Other sulfonylureas that may be used in the present invention are:

Amidosulfuron, azimsulfuron, bensulfuron, chlorimuron, chlorsulfuron, cinosulfuron, cyclosulfamuron, ethametsulfuon, ethoxysulfuron, flazasulfuron, flupyrsulfuon, foramsulfuron, halosulfuron, imazosulfuron, iodosulfuron, mesosulfuron, nicosulfuron, oxasulfuron, primisulfuron, prosulfuron, pyrazosulfuron rimsulfuron, sulfometuron, sulfosulfuron, thifensulfuron, triasulfuron, tribenuron, trifloxysulfuron, trflusulfuron, tritosulfuron; and all their common derivatives such methyl, meptyl, etc. esters.

Other similar agrochemicals (or their mixtures with or without fluoroxypyr and/or chlorpyrifos) as fluoroxypyr (for combination with sulfonylurea or not) may be selected from the group of all agrochemicals that are solid at room temperature and with a melting point at atmospheric pressure lower than 110° C.

Particularly interesant all triazole fungicides, in particular propiconazole, tebuconazole.

The sulfonylureas, for the purpose of protection against degradation may be well encapsulated according process using anionic substituted acrylic styrene polymers as dispersing agents, and optionally, encapsulated in such way that the encapsulation reaction takes place thanks to an emulsified catalyst (a polyamine). They may be as well microencapsulated according the European Patent Application EP 06006748, of the same Inventors and applied by GAT Formulation GmbH (reference incorporated for all this patent document in its totality for the purpose of microcapsules containing acetylene carbamide derivatives in the wall) and then create the WG.

The selection of coformulants for the creation of the CS, SC, ZC and WG formulations are in no way limited to the compounds mentioned in the examples: what is important is that the chemical class of chemicals remains as closer as possible. For example isocyanates as wall forming materials, polyamines or alkyltin fatty esthers as catalysts, sulfosuccinate addition before spray drying, etc. The wall forming materials may be composed of mixtures of isocyanates or mixtures of aromatic isocyanate(s), aliphatic isocyanate(s) and glicoluril derivatives having the four hydroxyl groups substituting the four nitrogen atoms of the five membered cycle replaced by a alkyloxyalkylen group, where alkylene has the meaning of methylen, ethylen, isopropylen, and alkyl the meaning methyl, ethyl, isopropyl.

It must be understood that when in this invention we refer to fluoroxypyr, we are also disclosing all compounds that are solid at room temperature and melt below 110° C.

The invention claimed is:

1. A composition containing microcapsules characterized in that the active ingredient(s) are selected alternatively from the groups:

(i) chlorpyrifos, or (ii) fluoroxypyr, or (iii) a combination of: (a) fluoroxypyr and (b) at least one sulfonylurea, wherein, either (a) is inside the microcapsules and (b) is(are) outside the microcapsules, or the reverse, or (iv) a combination of (b) at least one sulfonylurea and (c) one agrochemical compound whose melting point is below 110° C. and that is solid at room temperature, wherein (c) is inside the microcapsules and (b) is(are) outside the microcapsules, or the reverse, wherein the composition comprises a styrene acrylic polymer that is 1% to 45% by weight of the total weight of the composition;

wherein the microcapsules are made by the reaction of wall-forming materials comprising at least one aromatic isocyanate and a glycoluril derivative having the four hydrogens of the four nitrogen atoms substituted by an alkyloxyalkylene group, wherein alkylene has the meaning of methylene, ethylene or isopropylene, and alkyl has the meaning methyl, ethyl or isopropyl; and wherein the microcapsules have a particle size of 1 to 30 μm.

2. The composition of claim 1, wherein the wall of the microcapsules is made by the reaction of, in addition to the aromatic isocyanate and the glycoluril derivative, at least one aliphatic isocyanate.

3. The composition of claim 1, wherein the styrene acrylic copolymer is anionically substituted.

4. The composition of claim 1, wherein the composition contains a sulfosuccinate.

5. The composition of claim 1, wherein the composition comprises a suspension concentrate and the microencapsulated sulfonylureas are chosen from the group consisting of: amidosulfuron, azimsulfuron, bensulfuron, chlorimuron, chlorsulfuron, cinosulfuron, cyclosulfamuron, ethametsulfuon, ethoxysulfuron, flazasulfuron, flupyrsulfuon, foramsulfuron, halosulfuron, imazosulfuron, iodosulfuron, mesosulfuron, nicosulfuron, oxasulfuron, primisulfuron, prosulfuron, pyrazosulfuron rimsulfuron, sulfometuron, sulfosulfuron, thifensulfuron, triasulfuron, tribenuron, trifloxysulfuron, triflusulfuron and, tritosulfuron.

6. The composition of claim 1, wherein the composition comprises water dispersable granules and the microcapsules enclose fluoroxypyr.

7. The composition of claim 1, wherein the composition comprises water dispersable granules and the microcapsules enclose chlorpyrifos.

8. The composition of claim 1, wherein the composition comprises water dispersable granules and the microcapsules enclose diflufenican.

9. The composition of claim 1, wherein the composition comprises water dispersable granules and the active ingredient inside the microcapsule is fluoroxypyr and at least a sulfonylurea is outside of the microcapsules.

10. The composition of claim 1, wherein the composition comprises a capsule suspension and the microcapsules enclose fluoroxypyr.

11. The composition of claim 1, wherein the composition contains from 1% to 45% of an anionic styrene acrylic polymer, and, in the case of being a water dispersible concentrate, contains a sulfosuccinate in a concentration of 0.1% to 15% when calculated in the wet weight of the composition before the spray drying step.

12. A method of making the composition of claim 1, wherein the method comprises the following steps:

(a) providing an oil phase at about 75° C. containing the wall-forming materials, the active ingredient and a wall-forming catalyst, if the wall-forming catalyst is soluble in water;

(b) providing a water phase at about 75° C. containing an anionic substituted styrene acrylic polymer and an oil soluble emulsifier;

(c) mixing oil phase and the water phase to form a mixture;

(d) adding a dialkyltindilaureate catalyst to the mixture and emulsifying with high shear stress;

(e) maintaining the mixture at a constant temperature for about 2 hours;

(f) adding an anionic substituted styrene acrylic polymer and a sulfosuccinate to the mixture; and (g) spray drying the mixture at a temperature below the melting point of the active ingredient to thereby form the composition;

wherein, if the wall-forming catalyst is a polyamine catalyst insoluble in water, the catalyst is emulsified in the polyamine catalyst in the water phase.

* * * * *